(12) United States Patent
Jin et al.

(10) Patent No.: US 12,253,078 B2
(45) Date of Patent: Mar. 18, 2025

(54) PRESSURE-PUMP CARTRIDGE AND PRESSURE PUMP

(71) Applicant: MICRO-TECH (NANJING) CO., LTD., Nanjing (CN)

(72) Inventors: Hongyan Jin, Nanjing (CN); Hui Liu, Nanjing (CN); Jinwei Pang, Nanjing (CN); Derong Leng, Nanjing (CN); Changqing Li, Nanjing (CN); Jiefeng Xi, Nanjing (CN); Ning Li, Nanjing (CN); Chunjun Liu, Nanjing (CN); Zhi Tang, Nanjing (CN); Jianyu Wei, Nanjing (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 294 days.

(21) Appl. No.: 17/842,696

(22) Filed: Jun. 16, 2022

(65) Prior Publication Data
US 2022/0316471 A1 Oct. 6, 2022

Related U.S. Application Data

(63) Continuation of application No. PCT/CN2020/088315, filed on Apr. 30, 2020.

(30) Foreign Application Priority Data

Dec. 27, 2019 (CN) .......................... 201911377484.0

(51) Int. Cl.
*F04B 53/16* (2006.01)
*A61M 5/14* (2006.01)
(Continued)

(52) U.S. Cl.
CPC ......... *F04B 53/162* (2013.01); *A61M 5/1413* (2013.01); *A61M 5/14566* (2013.01);
(Continued)

(58) Field of Classification Search
CPC .. F04B 5/02; F04B 9/113; F04B 53/00; F04B 53/162; F04B 53/143; A61M 5/1413; A61M 5/14566; A61M 2205/123
See application file for complete search history.

(56) References Cited

U.S. PATENT DOCUMENTS

| 1,598,137 | A | | 8/1926 | Jun-Hyuk et al. |
| 3,990,816 | A | * | 11/1976 | Kohler .................. F04B 53/162 |
| | | | | 505/910 |

(Continued)

FOREIGN PATENT DOCUMENTS

| CN | 101300042 A | 11/2008 |
| CN | 101611227 A | 12/2009 |

(Continued)

OTHER PUBLICATIONS

The First Office Action dated Oct. 30, 2024 for Chinese Application No. 201911377484.0.

*Primary Examiner* — Peter J Bertheaud (57) ABSTRACT

Provided are a pressure-pump cartridge and a pressure pump, where the pressure-pump cartridge includes a cylinder, where the cylinder has a first chamber, a piston chamber and a second chamber hat are in communication in sequence, and the piston chamber is used for being in sealing fit with a piston. An end of the first chamber remote from the piston chamber is provided with a first opening allowing entry of the piston, and during installation, the piston enters the first chamber by the first opening and enters the piston chamber after passing through the first chamber, and meanwhile, the first chamber is configured to be in a clearance fit with the piston, such that the size of the first chamber is larger than that of the piston.

14 Claims, 7 Drawing Sheets

(51) Int. Cl.
  *A61M 5/145* (2006.01)
  *F04B 5/02* (2006.01)
  *F04B 9/113* (2006.01)
  *F04B 53/00* (2006.01)
  *F04B 53/14* (2006.01)

(52) U.S. Cl.
  CPC ................ *F04B 5/02* (2013.01); *F04B 9/113* (2013.01); *F04B 53/00* (2013.01); *F04B 53/143* (2013.01); *A61M 2205/123* (2013.01)

(56) References Cited

U.S. PATENT DOCUMENTS

| | | | |
|---|---|---|---|
| 5,156,537 A * | 10/1992 | Massinon | ................ F04B 5/02 |
| | | | 417/536 |
| 5,817,955 A | 10/1998 | Gherson et al. | |
| 8,915,399 B1 | 12/2014 | Nystrom | |
| 2018/0225423 A1 | 8/2018 | Bazargan | |

FOREIGN PATENT DOCUMENTS

| | | | |
|---|---|---|---|
| CN | 108136124 A | 6/2018 | |
| CN | 108302031 A | 7/2018 | |
| CN | 207920843 U | 9/2018 | |
| CN | 108883228 A | 11/2018 | |
| CN | 109915338 A | 6/2019 | |
| CN | 211174579 U | 8/2020 | |
| EP | 3138597 A1 | 3/2017 | |
| EP | 3335745 B1 | 12/2019 | |

\* cited by examiner

PRESSURE-PUMP CARTRIDGE AND PRESSURE PUMP

CROSS-REFERENCE TO RELATED APPLICATIONS

This application is a continuation of International Application No. PCT/CN2020/088315, filed on Apr. 30, 2020, which claims priority to the Chinese patent application No. CN201911377484.0 filed with the China National Intellectual Property Administration on Dec. 27, 2019 and entitled "Pressure-pump cartridge and Pressure Pump", both of which are hereby incorporated by reference in their entireties.

TECHNICAL FIELD

The present application relates to the technical field of medical devices, and in particular, to a pressure-pump cartridge and a pressure pump.

BACKGROUND

In some clinical operation, a pressure pump is required for injection. For example, in a submucosal resection, a pressure pump is required to achieve endoscopic submucous injection bulges.

In the pumping process of the pressure pump, in order to ensure a precise control of an infusion process, the sealing effect at the piston of the pressure pump is especially important. However, after the piston is installed in a current pressure pump, the problem of poor sealing effect at the piston often occurs, which in turn affects the precise control of the infusion process and increases the risk of surgery.

SUMMARY

An object of the present application includes, for example, providing a pressure-pump cartridge that can improve a phenomenon of poor sealing effect at the piston.

An object of the present application also includes providing a pressure pump including the above-mentioned pressure-pump cartridge.

The embodiments of the present application can be implemented as follows:

Embodiments of the present application provide a pressure-pump cartridge, which includes a cylinder, the cylinder has a first chamber, a piston chamber and a second chamber that are in communication in sequence; the cylinder has a first inner wall corresponding to the first chamber and a second inner wall corresponding to the second chamber; the first inner wall is provided with a first liquid inlet and a first liquid outlet, and the second inner wall is provided with a second liquid inlet and a second liquid outlet; and the piston chamber is configured to be in sealing fit with a piston; an end of the first chamber remote from the piston chamber has a first opening which is configured for entry of the piston, and the first chamber is configured to be in clearance fit with the piston.

In an implementation, the cylinder has a third inner wall corresponding to the piston chamber; a first guide surface is provided between the first inner wall and the third inner wall, and the first guide surface is configured to guide the piston from the first chamber into the piston chamber.

In an implementation, a distance from the first guide surface to an axis of the piston chamber gradually decreases along a direction in which the first chamber points to the piston chamber.

In an implementation, the first guide surface comprises a tapered surface, and a taper angle of the tapered surface is $\alpha$, with $30° \leq \alpha \leq 150°$.

In an implementation, both ends of the first guide surface are respectively connected with the first inner wall and the third inner wall.

In an implementation, both the first chamber and the piston chamber are cylindrical, a radial dimension corresponding to the first chamber is r1, and a radial dimension corresponding to the piston chamber is r2, with $0.2 \text{ mm} \leq (r1-r2)$.

In an implementation, the second chamber is configured to be in clearance fit with the piston.

In an implementation, the pressure-pump cartridge further comprises a first sealing structure disposed at the first opening, and the first sealing structure is connected with the cylinder to close the first opening.

In an implementation, the first sealing structure comprises a first connecting member and a first sealing member connected to the first connecting member; the first sealing member is located within the first chamber to close the first opening; and the first connecting member is fixedly connected to the cylinder.

In an implementation, the pressure-pump cartridge further comprises a fastener, the cylinder is provided with a first connecting hole, and the first connecting member is provided with a second connecting hole, the fastener fits with both the first connecting hole and the second connecting hole, so as to fix the first connecting member to the cylinder.

In an implementation, the numbers of the first connecting hole, the second connecting hole and the fastener are multiple, and the first connecting holes, the second connecting holes and the fasteners are disposed in a one-to-one correspondence, and the first connecting holes are evenly distributed around a circumferential direction of the first opening.

In an implementation, the cylinder further has a second opening communicating with the second chamber, and the pressure-pump cartridge further includes a second sealing structure disposed at the second opening; and the second sealing structure is connected with the cylinder to close the second opening.

In an implementation, the pressure-pump cartridge further comprises a first one-way valve, a second one-way valve, a third one-way valve and a fourth one-way valve;

the first one-way valve is installed at the first liquid inlet, the second one-way valve is installed at the first liquid outlet, the third one-way valve is installed at the second liquid inlet, and the fourth one-way valve is installed at the second liquid outlet.

Embodiments of the present application also provide a pressure pump. The pressure pump includes any one of the above-mentioned pressure-pump cartridges.

The beneficial effects of the pressure-pump cartridge and the pressure pump of the embodiments of the present application include, for example:

The embodiments of the present application provide a pressure-pump cartridge, which includes a cylinder. The cylinder has a first chamber, a piston chamber and a second chamber which are in communication in sequence. The cylinder also has a first inner wall corresponding to the first chamber and a second inner wall corresponding to the second chamber. The first inner wall is provided with a first liquid inlet and a first liquid outlet, and the second inner wall is provided with a second liquid inlet and a second liquid outlet. The piston chamber is configured to be in sealing fit with the piston, and when in use, the piston slides within the piston chamber to change volumes of spaces at both sides of the piston. When the piston moves along a direction in which the first chamber points to the second chamber, the fluid from the first liquid inlet flows into the first chamber, and the fluid within the second chamber flows out of the second liquid outlet; and when the piston moves along the direction in which the second chamber points to the first chamber, the fluid in the first chamber flows out of the first liquid outlet, and fluid at the second liquid inlet enters the second chamber; in this way, a continuous liquid supply of the cartridge is realized through an alternate liquid discharge from the two chambers.

An end of the first chamber remote from the piston chamber has a first opening configured for entry of the piston, and during installation, the piston passes through the first opening to enter the first chamber, and then passes through the first chamber to enter the piston chamber, and at the same time, the first chamber is disposed to be in clearance fit with the piston, so the size of the first chamber is larger than that of the piston, so as to avoid that the piston, when passing through the first chamber, is influenced by burrs formed due to the provision of the first liquid inlet and the first liquid outlet, which avoids the burrs to damage the piston, and thus avoids the problem of affecting the sealing performance of the piston, so that the sealing performance of the piston is guaranteed, and the sealing effect is excellent.

The embodiments of the present application also provide a pressure pump, which includes the above-mentioned pressure-pump cartridge. Since the pressure pump includes the above-mentioned pressure-pump cartridge, the pressure pump also has the beneficial effects of continuous liquid supply, guaranteed sealing performance of the piston and good sealing effect.

BRIEF DESCRIPTION OF DRAWINGS

In order to illustrate the technical solutions of the embodiments of the present application more clearly, the following briefly introduces the accompanying drawings that need to be used the embodiments. It should be understood that the following drawings only show some embodiments of the present application, and therefore it should not be regarded as a limitation of the scope, and for those of ordinary skill in the art, other related drawings can also be obtained according to these drawings without any creative effort.

Reference numbers: 10—pressure-pump cartridge; 100—cylinder; 110—working chamber; 111—first chamber; 112—piston chamber; 113—second chamber; 114—first inner wall; 115—second inner wall; 116—third inner wall; 117—first guide surface; 1171—tapered surface; 1172—arc surface; 118—second guide surface; 121—first liquid inlet; 122—first liquid outlet; 123—second liquid inlet; 124—second liquid outlet; 125—first opening; 126—second opening; 131—first connecting hole; 132—snap-fit groove; 133—third opening; 134—first installing hole; 210—first sealing structure; 211—first sealing member; 212—first connecting member; 213—second connecting hole; 220—second sealing structure; 221—second sealing member; 222—second connecting member; 230—fastener; 300—piston structure; 310—piston rod; 320—piston; 321—piston body; 322—rubber ring; 400—cover; 411—liquid inlet channel; 412—liquid outlet channel; 413—snap-fit protrusion; 414—second installing hole; 511—first one-way valve; 512—second one-way valve.

DESCRIPTION OF EMBODIMENTS

In order to make the purposes, technical solutions and advantages of the embodiments of the present application more clear, the technical solutions of the embodiment of the present application will be clearly and completely described below with reference to the drawings in the embodiment of the present application. Obviously, the described embodiments are part of the embodiments of the present application, but not all of the embodiments. The components of the embodiments of the present application generally described and illustrated in the drawings herein may be arranged and designed in a variety of different configurations.

Thus, the following detailed description of the embodiments of the application provided in the accompanying drawings is not intended to limit the scope of the present application as claimed, but is merely representative of selected embodiments of the present application. Based on the embodiments in the present application, all other embodiment obtained by those of ordinary skill in the art without paying creative efforts will fall within the protection scope of the present application.

It should be noted that similar numerals and letters refer to similar items in the following figures, so once an item is defined in one figure, it does not require further definition and explanation in subsequent figures.

In the description of the present application, it should be noted that, if terms "upper", "lower", "inner", "outer" and the like appear, they indicate an orientation or position relationship, they are based on an orientation or position relationship shown in the drawings, or they are an orientation or position relationship usually placed when the product of the present application is used. The orientation or position relationship is only for the convenience of describing this application and simplifying the description, rather than indicating or implying that the device or element referred to must have a specific orientation or must be constructed and operated in a specific orientation, and therefore it should not be construed as a limitation of this application.

In addition, if terms "first", "second" and the like appear, they are only used to distinguish the description, and should not be construed as indicating or implying relative importance.

It should be noted that the features in the embodiments of the present application may be combined with each other without conflict.

Figure 1:
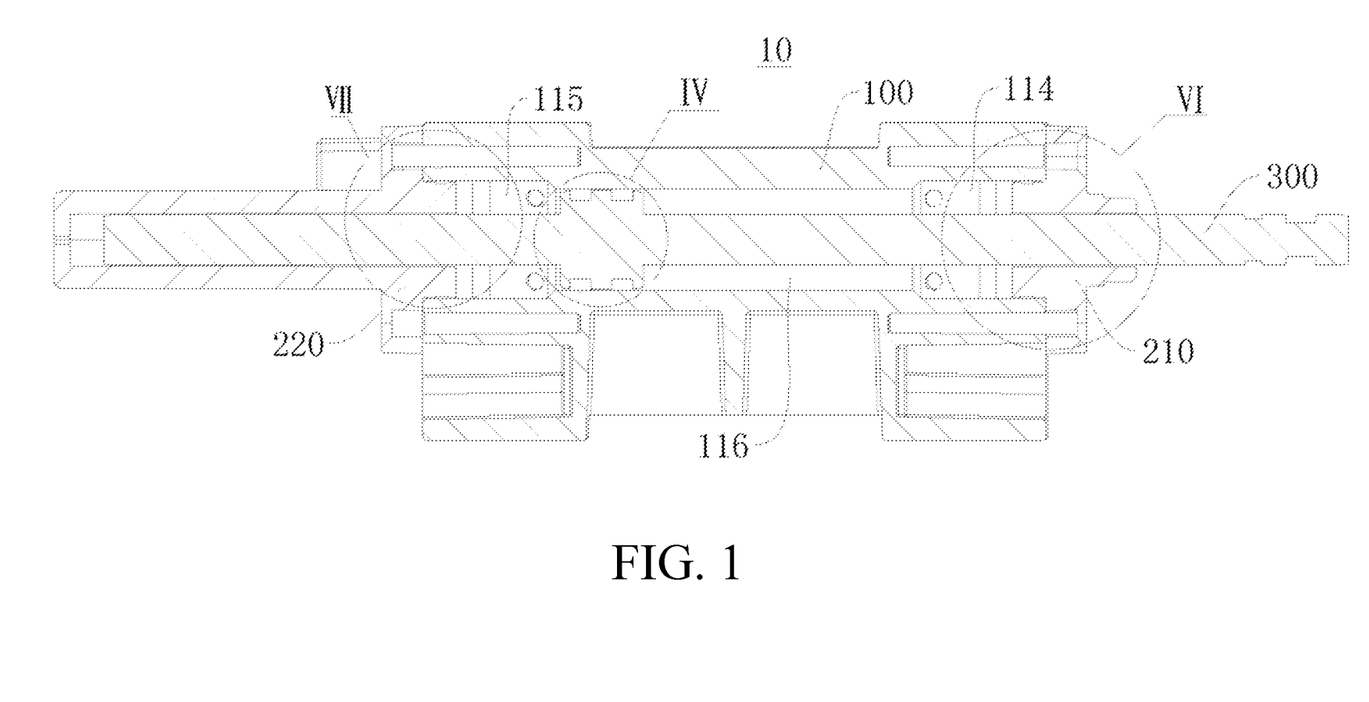
FIG. 1 is a schematic cross-sectional structural diagram of a pressure-pump cartridge provided in an embodiment of the present application from a first perspective.
Figure 2:
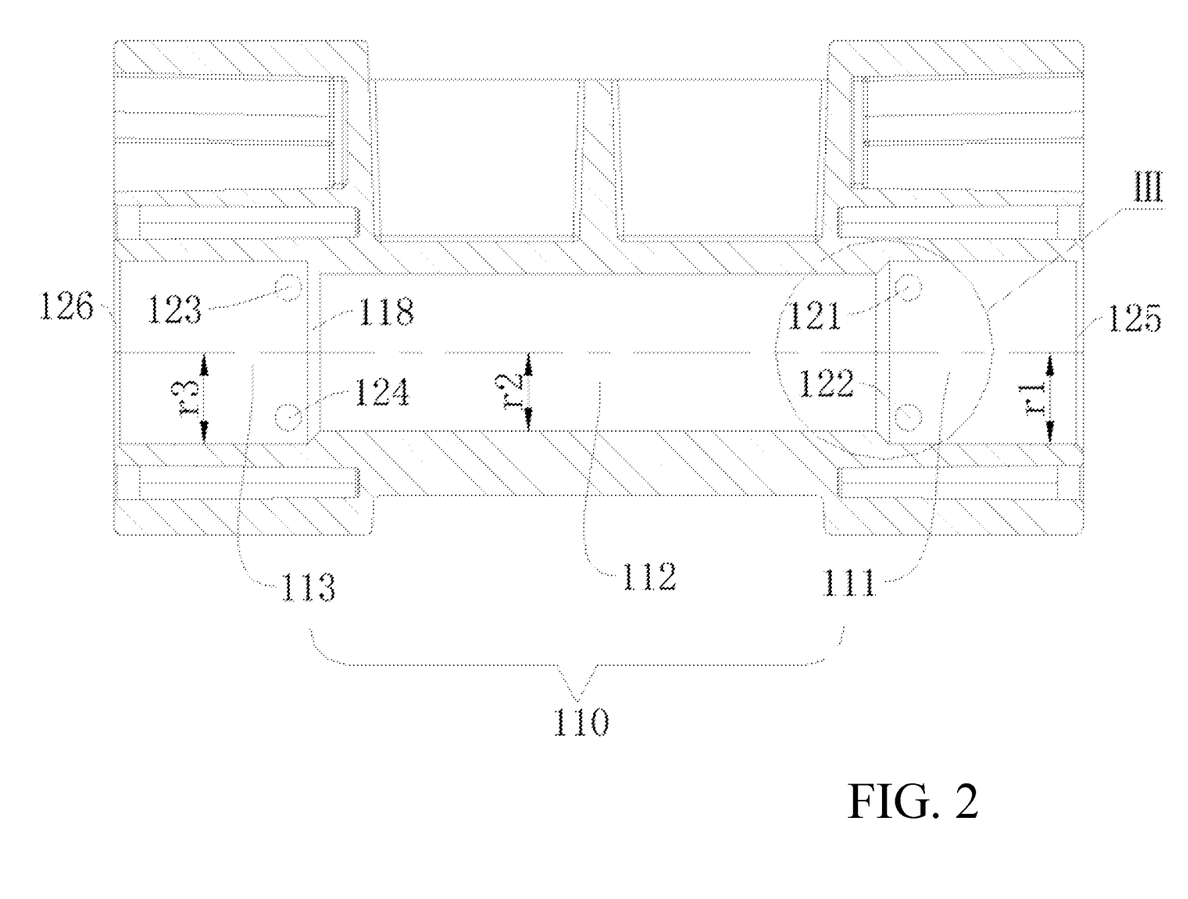
FIG. 2 is a schematic cross-sectional structural diagram of a cylinder in a pressure-pump cartridge provided by an embodiment of the present application.

FIG. 1 is a schematic cross-sectional structural diagram of pressure-pump cartridge 10 provided in an embodiment of the present application from a first perspective and FIG. 2 is a schematic cross-sectional structural diagram of a cylinder 100 in pressure-pump cartridge 10 provided by an embodiment of the present application. Please refer to FIG. 1 and FIG. 2 in combination, this embodiment provides pressure-pump cartridge 10, and correspondingly, provides a pressure pump (not shown in the figures).

The pressure-pump cartridge 10 includes a cylinder 100. The cylinder 100 has a first chamber 111, a piston chamber 112 and a second chamber 113 which are in communication in sequence. The cylinder 100 also has a first inner wall 114 corresponding to the first chamber 111 and a second inner wall 115 corresponding to the second chamber 113. The first inner wall 114 is provided with a first liquid inlet 121 and a first liquid outlet 122, and the second inner wall 115 is provided with a second liquid inlet 123 and a second liquid outlet 124. The piston chamber 112 is configured to be in sealing fit with the piston 320, and when in use, the piston 320 slides within the piston chamber 112 to change volumes of the spaces at both sides of the piston 320. When the piston 320 moves along a direction in which the first chamber 111 points to the second chamber 113, the fluid from the first liquid inlet 121 flows into the first chamber 111, and the fluid within the second chamber 113 flows out of the second liquid outlet 124; and when the piston 320 moves along a direction in which the second chamber 113 points to the first chamber 111, the fluid in the first chamber 111 flows out of the first liquid outlet 122, and fluid at the second liquid inlet 123 enters the second chamber 113; in this way, a continuous liquid supply of the pressure-pump cartridge 10 is realized through an alternate liquid discharge from the two chambers.

An end of the first chamber 111 remote from the piston chamber 112 has a first opening 125 configured for entry of the piston 320, and during installation, the piston 320 passes through the first opening 125 to enter the first chamber 111, and then passes through the first chamber 111 to enter the piston chamber 112, and at the same time, the first chamber 111 is disposed to be in clearance fit with the piston 320, so the size of the first chamber 111 is larger than that of the piston 320, so as to avoid that the piston 320, when passing through the first chamber 111, is influenced by burrs formed due to the provision of the first liquid inlet 121 and the first liquid outlet 122, which avoids the burrs to damage the piston 320, and thus avoids the problem of affecting the sealing performance of the piston 320, so that the sealing performance of the piston 320 is guaranteed, and the sealing effect is excellent.

The pressure pump includes the above-mentioned pressure-pump cartridge 10, and the pressure pump also includes a liquid inlet pipe (not shown in the figures) and a liquid outlet pipe (not shown in the figures), and the liquid inlet pipe is in communication with both the first liquid inlet 121 and the second liquid inlet 123, so as to supply liquid to the first chamber 111 and the second chamber 113 with the movement of the piston 320; the liquid outlet pipe is in communication with both the first liquid outlet 122 and the second liquid outlet 124, so that the liquid in the first chamber 111 and the second chamber 113 can be outputted with the movement of the piston 320. Since the first chamber 111 and the second chamber 113 discharge liquid alternately, a continuous liquid discharge of the liquid outlet pipe is realized.

The pressure-pump cartridge 10 provided in this embodiment is further described below:

Please refer to FIG. 1 and FIG. 2 in combination, in this embodiment, the pressure-pump cartridge 10 includes a cylinder 100 and a piston 320, the cylinder 100 has a working chamber 110 therein, and the piston 320 is slidably fitted with the working chamber 110, so that the working chamber 110 is divided into two independent sub-chambers, the two sub-chambers are a first sub-chamber and a second sub-chamber respectively, and the volumes of the first sub-chamber and the second sub-chamber are changed by the sliding of the piston 320.

Specifically, the working chamber 110 includes a first chamber 111, a piston chamber 112 and a second chamber 113 which are connected in sequence, and the cylinder 100 has a first inner wall 114 corresponding to the first chamber 111, a second inner wall 115 corresponding to the second chamber 113 and a third inner wall 116 corresponding to the piston chamber 112. After the piston 320 is installed into the working chamber 110, the piston 320 is slidably fitted with the piston chamber 112 and the piston 320 is in sealing contact with the third inner wall 116, the first sub-chamber formed by the division via the piston 320 is formed by the first chamber 111 and a part of the piston chamber 112 located on a side of the piston 320 close to the first chamber 111, and the second sub-chamber formed by the division via the piston 320 is formed by the second chamber 113 and a part of the piston chamber 112 located on a side of the piston 320 close to the second chamber 113.

The first inner wall 114 is provided with a first liquid inlet 121 and a first liquid outlet 122, and during the operation of the pressure pump, the piston 320 always slides back and forth within the piston chamber 112, so the first liquid inlet 121 and the first liquid outlet 122 are always in communication with the first sub-chamber; the second inner wall 115 is provided with a second liquid inlet 123 and a second liquid outlet 124, and during the operation of the pressure pump, the piston 320 always slides back and forth within the piston chamber 112, so that the second liquid inlet 123 and the second liquid outlet 124 are always in communication with the second sub-chamber. When the piston 320 moves towards a direction close to the first chamber 111, the volume of the first sub-chamber becomes smaller, the fluid in the first sub-chamber is squeezed to flow out of the first liquid outlet 122, and the volume of the second sub-chamber becomes larger, which causes the pressure in the second sub-chamber to decrease, and the fluid in the second liquid inlet 123 flows into the second sub-chamber under pressure; when the piston 320 moves towards a direction close to the second chamber 113, the volume of the second sub-chamber becomes smaller, the fluid in the second sub-chamber is squeezed to flow out of the second liquid outlet 124, and the volume of the first sub-chamber becomes larger, which causes the pressure in the first sub-chamber to decrease, the fluid in the first liquid inlet 121 flows into the first sub-chamber under pressure.

In an implementation, the first chamber 111, the piston chamber 112 and the second chamber 113 are each cylindrical, and the first chamber 111, the piston chamber 112 and the second chamber 113 are coaxially arranged. It should be noted that the shapes and relative positions of the first chamber 111, the piston chamber 112 and the second chamber 113 are not limited here, it can be understood that in other embodiments, the shape and relative position relationship of each chamber can also be specifically set according to needs of users, for example, the first chamber 111 is disposed to be square, or the second chamber 113 is disposed eccentrically relative to the piston chamber 112.

An end of the first chamber 111 remote from the piston chamber 112 has a first opening 125, and during installation, the piston 320 enters the first chamber 111 from the first opening 125, passes through the first chamber 111 and then enters the piston chamber 112, and then is in sealing fit with the piston chamber 112. The first chamber 111 is in clearance fit with the piston 320, that is, a radial dimension r1 corresponding to the first chamber 111 is larger than a radial dimension r2 corresponding to the piston chamber 112. It should be noted that, in the description of this embodiment, the radial dimension is a radial dimension of a corresponding cylinder. Since the first chamber 111 is in clearance fit with the piston 320, during the movement of the piston 320 to the piston chamber 112 along the axial direction of the first chamber 111, there is a gap between the piston 320 and the first inner wall 114, that is, the piston 320 is not in contact with the first inner wall 114, so that the burrs generated by the provision of the first liquid inlet 121 and the first liquid outlet 122 on the first inner wall 114 can be effectively avoided from contacting with the piston 320, which also prevents the damage to the piston 320 due to contact with the burrs, thereby avoiding problems of affecting the sealing performance.

In order to ensure that the piston 320 is not damaged due to contact with the burrs during the installation process, further, 0.2 mm≤(r1−r2), in an implementation, (r1−r2)=0.2 mm, 0.5 mm or 0.8 mm, etc. It can be understood that in other embodiments, the difference between r1 and r2 can also be disposed to other values according to needs, as long as it can be ensured that r1 is greater than r2, and the piston 320 will not be damaged by burrs during installation and affecting the sealing effect.

Figure 3:
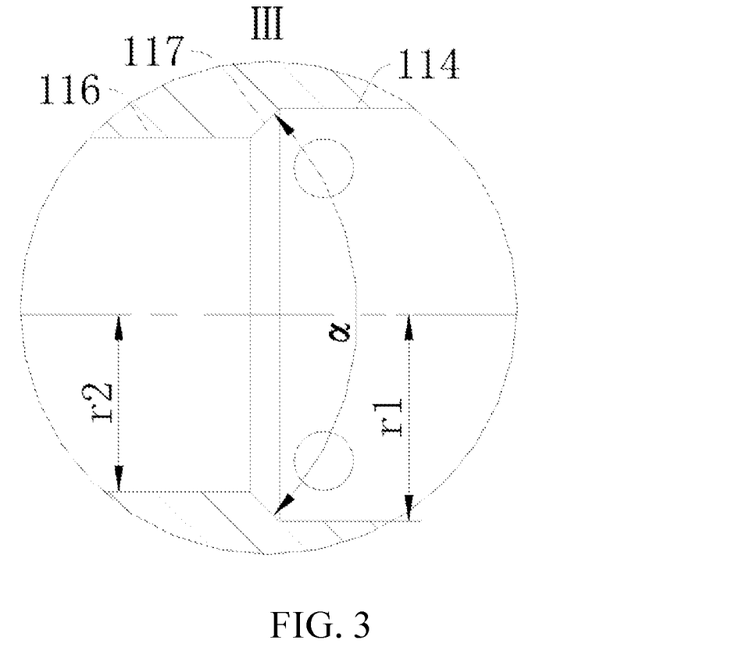
FIG. 3 is an enlarged schematic diagram of a local structure at III in FIG. 2.

FIG. 3 is an enlarged schematic diagram of a local structure at III in FIG. 2. Referring to FIG. 1-FIG. 3 in combination, in this embodiment, the cylinder 100 further has a first guide surface 117 provided between the first inner wall 114 and the third inner wall 116, and the first guide surface 117 is configured to guide the piston 320 from the first chamber 111 into the piston chamber 112. Specifically, along a direction in which the first chamber 111 points to the piston chamber 112 (i.e., left-right direction as shown in FIG. 2), a distance from the first guide surface 117 to an axis of the piston chamber 112 gradually decreases. By providing the first guide surface 117 to guide the installation of the piston 320, the installation of the piston 320 is more convenient and the damage to the piston 320 is reduced.

Figure 4:
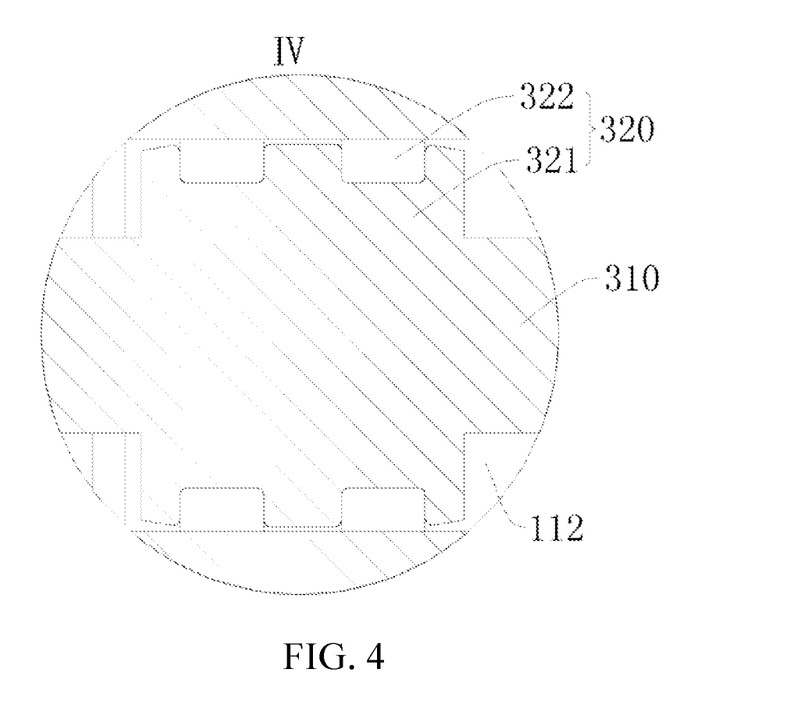
FIG. 4 is an enlarged schematic diagram of a local structure at IV in FIG. 1.

FIG. 4 is an enlarged schematic diagram of a local structure at IV in FIG. 1. Referring to FIG. 4, the pressure-pump cartridge 10 further includes a piston structure 300. Specifically, the piston structure 300 includes a piston rod 310 and a piston 320 connected to the piston rod 310. The piston 320 includes a piston body 321 and a rubber ring 322 mounted on the piston body 321. The piston body 321 is a protrusion structure formed by the peripheral surface located in the middle of the piston rod 310 protruding radially outward, and the piston body 321 has a sealing groove thereon, and the rubber ring 322 is snapped in the sealing groove, so as to be connected with the piston body 321, meanwhile the outer end of the rubber ring 322 is provided to protrude out of the peripheral surface of the piston body 321. It can be understood that in other embodiments, the rubber ring 322 can also be fixed to the piston body 321 in other ways, such as glue.

After installation, the rubber ring 322 is squeezed and deformed by the third inner wall 116 to be in sealing fit with the third inner wall 116, so as to realize the sealing fit of the piston 320 with the piston chamber 112, and an end of the piston rod 310 extends out from the first chamber 111, such that the piston rod 310 is connected to a power structure (not shown) located outside the cylinder 100, and the power structure drives the piston rod 310 to reciprocate along its own axis, thereby driving the piston 320 to slide back and forth relative to the third inner wall 116, so as to achieve pumping of the fluid. The first guide surface 117 is provided to guide the piston 320 to be installed into the piston chamber 112, thereby guiding the rubber ring 322 to gradually deform during the installation process, which not only reduces the difficulty of installation, but also reduces damage to the rubber ring 322.

Since both the first chamber 111 and the piston chamber 112 are cylindrical, in an implementation, the first guide surface 117 is a tapered surface, the radial dimension of the first guide surface 117 gradually reduces along the direction in which the first chamber 111 points to the piston chamber 112, so when the piston 320 moves into the piston chamber 112 through the first guide surface 117, the rubber ring 322 is gradually deformed by the compression of the first guide surface 117 until it is deformed to be matched with the first inner wall 114 and then enters into the piston chamber 112 smoothly.

Figure 5:
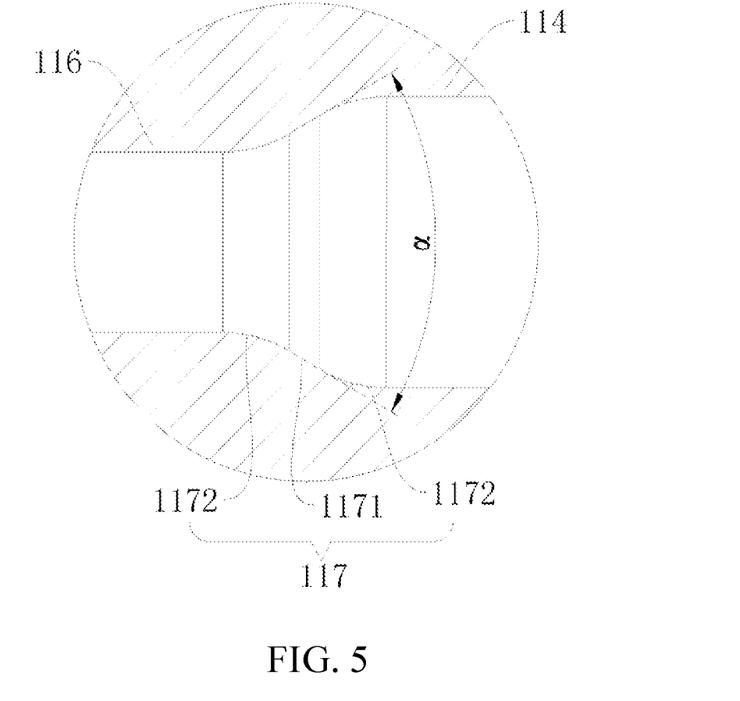
FIG. 5 is a schematic structural diagram of another first guide surface in a pressure-pump cartridge provided by an embodiment of the present application.

It should be noted that a specific shape of the first guide surface 117 is not limited here, it can be understood that in other embodiments, the first guide surface 117 can also be specifically disposed as required, for example, the first guide surface 117 can be disposed as an arc surface or as being formed by a combination of an arc surface 1172 and a tapered surface 1171 (as shown in FIG. 5), and along a direction in which the first chamber 111 points to the piston chamber 112, a distance from the first guide surface 117 to an axis (i.e., the axis of the piston chamber 112) of the working chamber 110 is gradually reduced, so long as the piston 320 can be guided into the piston chamber 112. It should also be noted that the first guide surface 117 shown in FIG. 5 includes the tapered surface 1171 and two arc surfaces 1172, and the two arc surfaces 1172 are located on two sides of the tapered surface 1171 respectively. It can be understood that in other embodiment, the first guide surface 117 can also be configured to include one tapered surface 1171 and one arc surface 1172, and the arc surface 1172 is located between the tapered surface 1171 and the first inner wall 114 or the arc surface 1172 is located between the tapered surface 1171 and third inner wall 116, or the first guide surface is configured to include two arc surfaces 1172, and centers of the two arc surfaces 1172 are located on two sides of the first guide surface, respectively.

Further, a taper angle of the taper surface (that is, an angle formed by two waists of the isosceles trapezoid formed by the projection of the first guide surface 117 on the cross-section shown in FIG. 2 and FIG. 3) is α, 30°≤α≤150°, in an implementation α=30°, 90° or 150°.

Further, both ends of the first guide surface 117 are connected to the first inner wall 114 and the third inner wall 116 respectively, and along a direction from the first chamber 111 to the piston chamber 112, the first inner wall 114, the first guide surface 117 and the third inner wall 116 are connected in sequence, a radial dimension of a large end of the first guide surface 117 is the same as a radial dimension of the first inner wall 114, and a radial dimension of a small end of the first guide surface 117 is the same as a radial dimension of the third inner wall 116. By disposing the first guide surface 117 at the connection between the first inner wall 114 and the third inner wall 116, the disposing of the first guide surface 117 is more convenient. It can be understood that in other embodiments, the position of the first guide surface 117 can also be disposed as required, for example, the first guide surface 117 is disposed as a surface that protrudes from an end of the third inner wall 116 close to the first inner wall 114 and approaches the third inner wall 116.

Referring to FIG. 2, in this embodiment, the second chamber 113 is also in clearance fit with the piston 320, in an implementation, a radial dimension corresponding to the second chamber 113 is r3, r3=r1, so as to facilitate ensuring that the second chamber 113 has the same volume as the first chamber 111, thereby facilitating precise control of the injection. Further, the cylinder 100 also has a second guide surface 118 disposed between the second inner wall 115 and the third inner wall 116. Specifically, the second guide surface 118 has the same shape and size as the first guide surface 117, so that a space correspondingly formed by the second guide surface 118 and located between the second chamber 113 and the piston chamber 112 is equal in size as a space correspondingly formed by the first guide surface 117 and located between the first chamber 111 and the piston chamber 112.

Further, the cylinder 100 also has a second opening 126 communicating with the second chamber 113, and the second opening 126 is located at an end of the second chamber 113 remote from the piston chamber 112. Due to the provision of the second opening 126, when the piston 320 is installed, the piston 320 can also be installed into the second chamber 113 from the second opening 126, passes through the second chamber 113, and then is installed into the piston chamber 112 under the guidance of the second guide surface 118. The installation of the piston 320 is more convenient.

Figure 6:
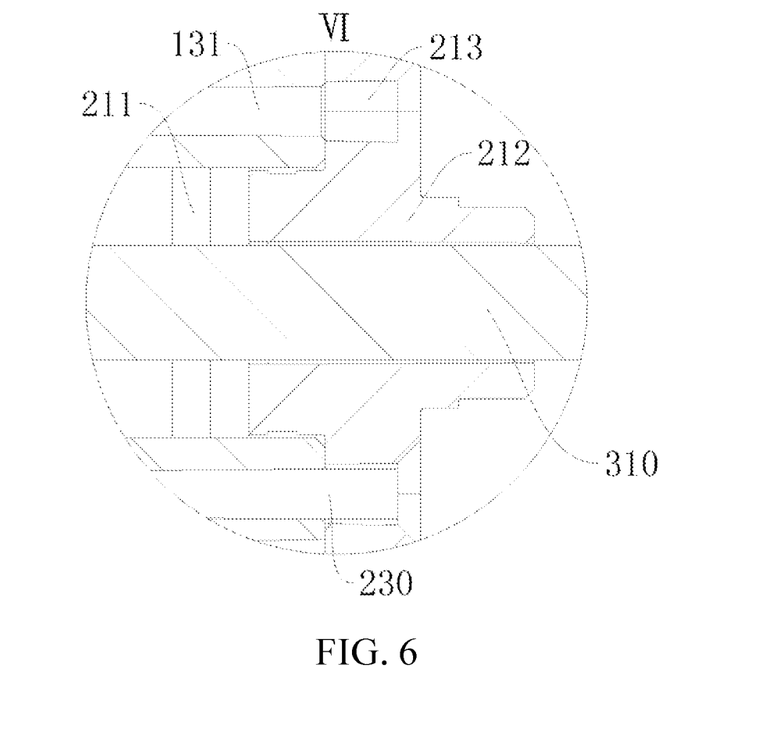
FIG. 6 is an enlarged schematic diagram of a local structure at VI in FIG. 1.

FIG. 6 is an enlarged schematic diagram of a local structure at VI in FIG. 1. Please refer to FIG. 1 and FIG. 6 in combination, in this embodiment, the pressure-pump cartridge 10 further includes a first sealing structure 210 disposed at the first opening 125, and the first sealing structure 210 is connected with the cylinder 100 to close the first opening 125, so as to avoid fluid leakage from the first opening 125 during the working process.

In an implementation, the first sealing structure 210 includes a first connecting member 212 and a first sealing member 211 connected to the first connecting member 212. The first connecting member 212 is fixedly connected with the cylinder 100 so as to fix the first sealing structure 210 to the cylinder 100. The first sealing member 211 is located within the first chamber 111 and in sealing fit with the first inner wall 114, thereby closing the first opening 125. By disposing the first sealing member 211 within the first chamber 111 and meanwhile achieving sealing by the sealing fit between the first sealing member 211 and the first inner wall 114, the sealing effect is improved.

Further, the pressure-pump cartridge 10 also includes a fastener 230. A first connecting hole 131 is formed on the cylinder 100, and a second connecting hole 213 is formed on the first connecting member 212. The fastener 230 is matched with both the first connecting hole 131 and the second connecting hole 213, thereby fixing the first connecting member 212 to the cylinder 100. Specifically, the fastener 230 is a screw, the first connecting hole 131 is a threaded hole, and the screw passes through the second connecting hole 213 and then is screwed into the first connecting hole 131, thereby realizing a fixed connection between the first connecting member 212 and the cylinder 100. It can be understood that in other embodiments, other types of fastener 230 such as pin may also be used to fix the first connecting member 212 to the cylinder 100.

It should be noted that the connection method between the first connecting member 212 and the cylinder 100 is not limited here, it can be understood that in other embodiments, other methods for example gluing, snap-connection, etc., can also be selected as required to fix the first connecting member 212 to the cylinder 100, so long as the reliability of the connection between the first connecting member 212 and the cylinder 100 can be guaranteed.

Further, the numbers of the first connecting hole 131, the second connecting hole 213 and the fastener 230 are all multiple, and the first connecting holes 131, the second connecting holes 213 and the fasteners 230 are disposed in a one-to-one correspondence. That is, each first connecting hole 131 corresponds to one second connecting hole 213, and one of the fasteners 230 fits with this first connecting hole 131 and this second connecting hole 213. By the fastening function of the multiple fasteners 230, the connection between the first connecting member 212 and the cylinder 100 is more reliable. At the same time, the multiple first connecting holes 131 are evenly distributed along the circumferential direction of the first opening 125. In an implementation, the number of the first connecting holes 131 is four, and correspondingly, the numbers of the second connecting holes 213 and the fasteners 230 are also four. It can be understood that in other embodiments, the numbers of the first connecting holes 131, the second connecting holes 213 and the fasteners 230 can be specifically disposed as required, for example, the numbers of the first connecting holes 131, the second connecting holes 213 and the fasteners 230 are disposed as three or six and so on.

Further, the first sealing structure 210 also has a through hole for the piston rod 310 to pass through, specifically, the through hole is provided to pass through the first connecting member 212 and the first sealing member 211, the piston rod 310, after installation, passes out of the first chamber 111 from the through hole, to connect with the power structure outside the cylinder 100, and then reciprocate under the drive of the power structure. The first sealing member 211 is in sealing fit with the piston rod 310, thereby preventing the fluid in the cylinder 100 from leaking from the through hole, and thus the sealing effect of the pressure-pump cartridge 10 is better.

Figure 7:
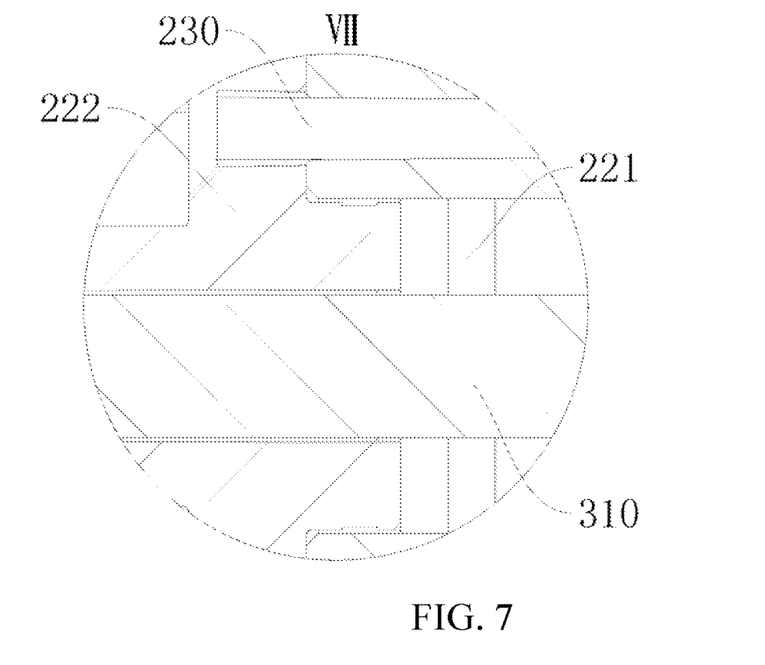
FIG. 7 is an enlarged schematic diagram of a local structure at VII in FIG. 1.

FIG. 7 is an enlarged schematic diagram of a local structure at VII in FIG. 1. Please refer to FIG. 1 and FIG. 6 in combination, in this embodiment, the pressure-pump cartridge 10 further includes a second sealing structure 220 disposed at the second opening 126, and the second sealing structure 220 is connected with the cylinder 100 to close the second opening 126, so as to prevent the fluid in the cylinder 100 from leaking from the second opening 126. The second sealing structure 220 is the same as the first sealing structure 210. Specifically, the second sealing structure 220 includes a second connecting member 222 and a second sealing member 221 connected with the second connecting member 222. The second connecting member 222 is fixedly connected with the cylinder 100, so as to realize the fixing between the second sealing structure 220 and the cylinder 100. The second sealing member 221 is located within the second chamber 113, and is in sealing fit with the second inner wall 115, so as to close the second opening 126, and the sealing effect is excellent. Further, the second connecting member 222 and the cylinder 100 are fixed by the fastener 230.

It should be noted that the specific structure of the second sealing structure 220 is not limited here, it can be understood that, in other embodiments, other structures can also be used to seal the second opening 126 as required, so long as the sealing effect can be guaranteed.

Figure 8:
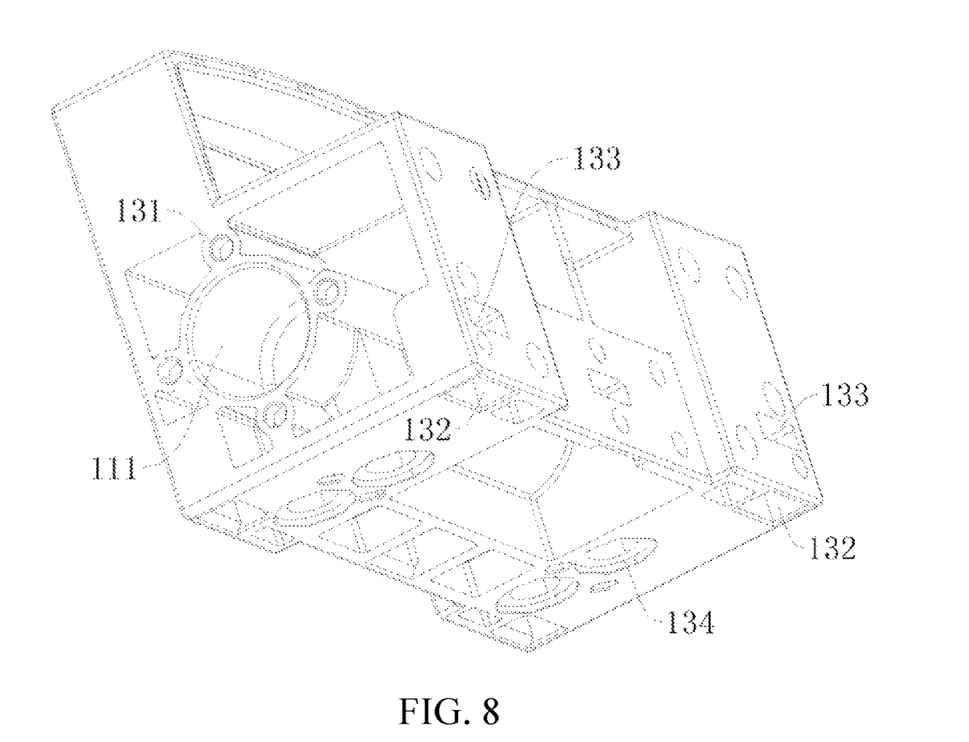
FIG. 8 is a schematic structural diagram of a cylinder in a pressure-pump cartridge provided by an embodiment of the present application.
Figure 9:
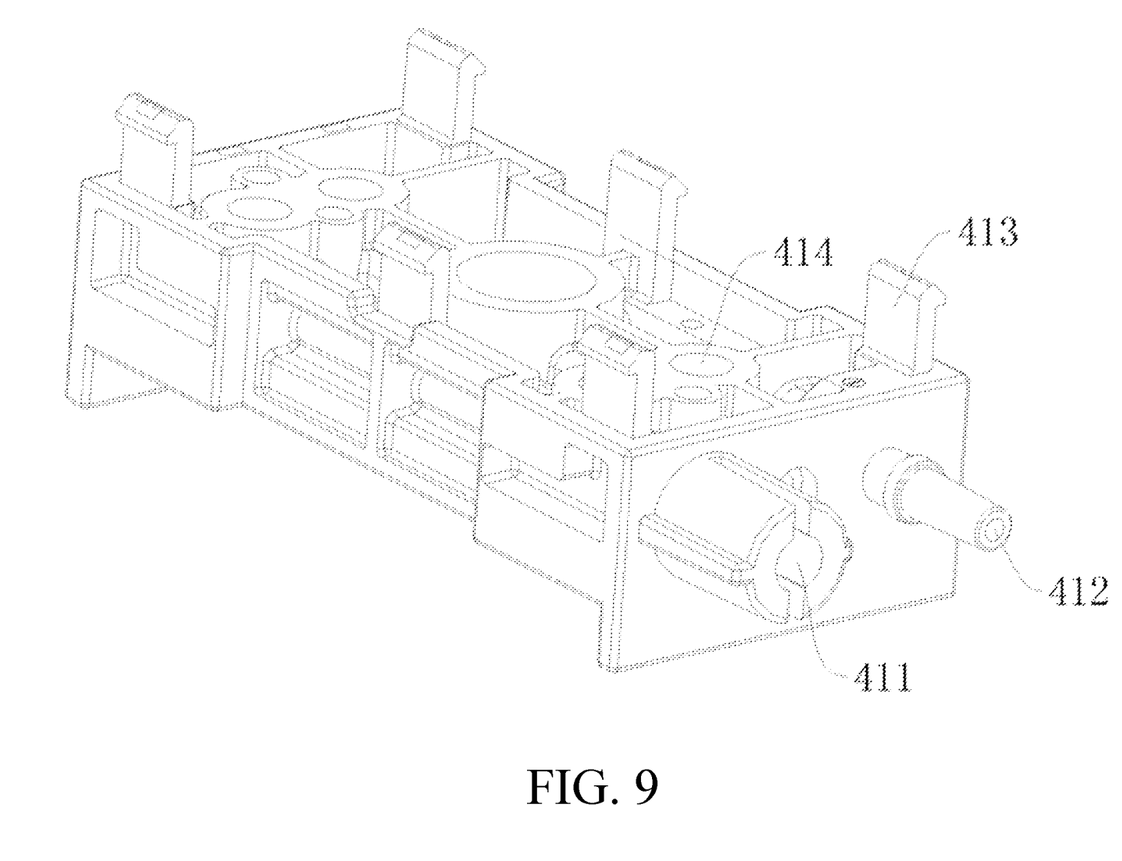
FIG. 9 is a schematic structural diagram of a cover in a pressure-pump cartridge provided by an embodiment of the present application.
Figure 10:
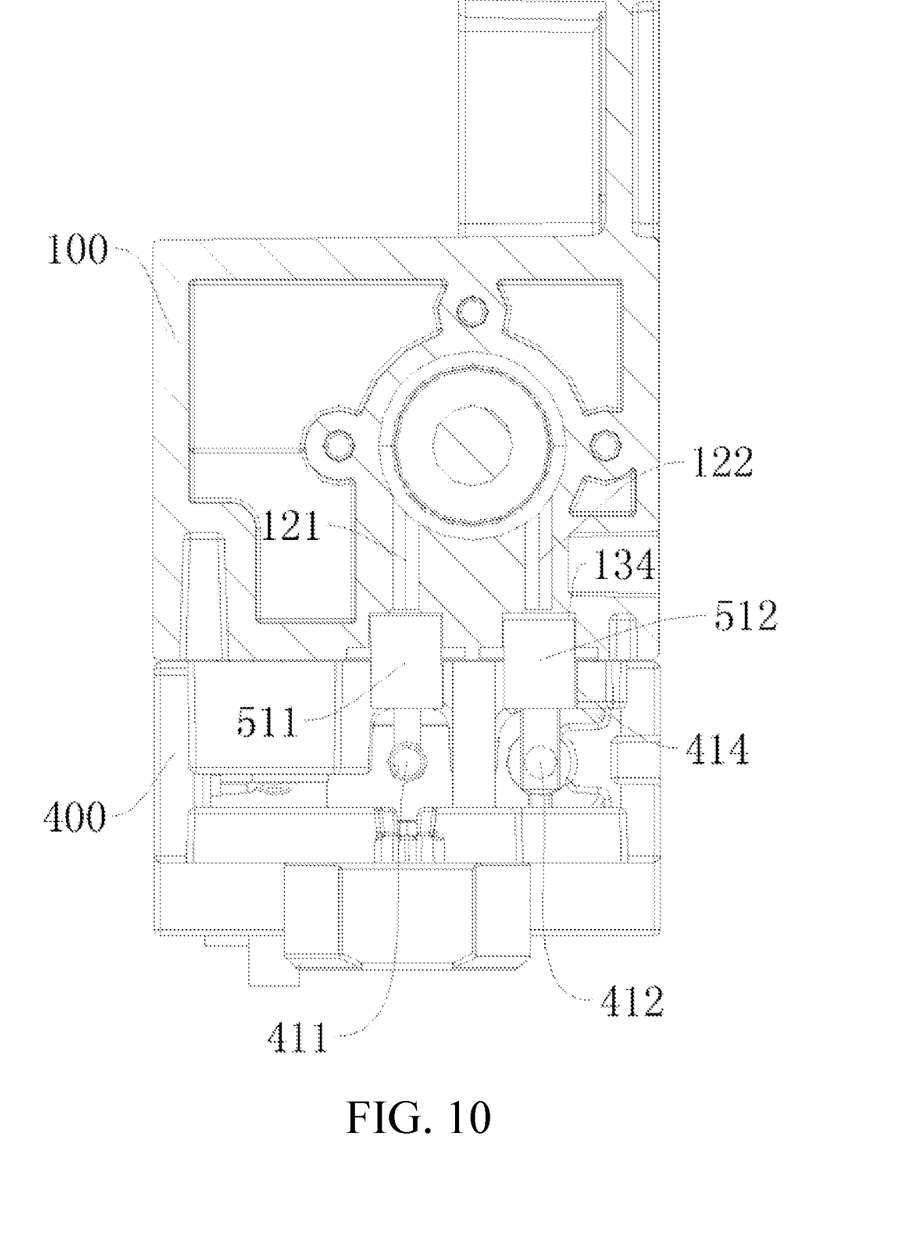
FIG. 10 is a schematic cross-sectional structural diagram of a pressure-pump cartridge provided in an embodiment of the present application from a second perspective.

FIG. 8 is a schematic structural diagram of the cylinder 100 in the pressure-pump cartridge 10 provided by this embodiment, FIG. 9 is a schematic structural diagram of a cover 400 in the pressure-pump cartridge 10 provided by this embodiment, FIG. 10 is a schematic cross-sectional structural diagram of the pressure-pump cartridge 10 provided by this embodiment from a second perspective. Please refer to FIG. 8 to FIG. 10 in combination, in this embodiment, the pressure-pump cartridge 10 further includes a cover 400 connected below the cylinder 100. The cover 400 has a liquid inlet channel 411 and a liquid outlet channel 412, and after the cylinder 100 is installed to the cover 400, the liquid inlet channel 411 communicates with both the first liquid inlet 121 and the second liquid inlet 123, and the liquid outlet channel 412 communicates with both the first liquid outlet 122 and the second liquid outlet 124. When in use, a liquid inlet pipe of the pressure pump is in communication with the liquid inlet channel 411 to provide the liquid for the first sub-chamber and the second sub-chamber with the movement of the piston 320, and the liquid outlet pipe of the pressure pump is in communication with the liquid outlet channel 412, and with the movement of the piston 320, the fluid in the first sub-chamber and the second sub-chamber alternately enters the liquid outlet channel 412 and enters the liquid outlet pipe by the liquid outlet channel 412 to realize continuous liquid supply.

Further, the cylinder 100 is provided with a snap-fit groove 132, and the cover 400 is provided with a snap-fit protrusion 413 that is in snap-connection with the snap-fit groove 132, the cylinder 100 is connected with and fixed to the cover 400 by the snap-connection between the snap-fit protrusion 413 and the snap-fit groove 132. Specifically, further, snap-fit groove 132 is provided on the lower side of the cylinder 100, and an opening that fits with the snap-fit protrusion 413 is provided on the side wall of the snap-fit groove 132, and the opening is a third opening 133, the third opening 133 are disposed through the side wall of the cylinder 100, and when snap-connecting, the snap-fit protrusion 413 extends from the lower end of the cylinder 100 into the snap-fit groove 132 and opens and closes at the third opening 133, thereby realizing the snap-fit engagement and fixation between the cylinder 100 and the cover 400.

Further, the numbers of both the snap-fit groove 132 and the snap-fit protrusion 413 are multiple, and the snap-fit groove 132 and the snap-fit protrusion 413 are connected in one-to-one correspondence, and a snap-fit connection between the multiple snap-fit grooves 132 with the multiple snap-fit protrusions 413 makes the connection and positioning between the cylinder 100 and the cover 400 more reliable. In an implementation, the number of the snap-fit protrusions 413 is six, and the six snap-fit protrusions 413 are disposed in an array. Correspondingly, the number of the snap-fit grooves 132 is six, and the positions thereof are disposed corresponding to the snap-fit protrusions 413. It can be understood that, in other embodiments, the numbers of the snap-fit protrusions 413 and the snap-fit grooves 132 can also be specifically disposed according to the needs of the user, for example, the numbers of both the snap-fit protrusions 413 and the snap-fit grooves 132 are disposed to four or eight, etc.

Further, the pressure-pump cartridge 10 further includes a one-way valve. Specifically, the number of the one-way valve is four, and the four one-way valves are first one-way valve 511, second one-way valve 512, third one-way valve (not shown) and fourth one-way valve (not shown), respectively. The first one-way valve 511 is provided corresponding to the first liquid inlet 121, so that the fluid at the first liquid inlet 121 flows unidirectionally in a direction from the liquid inlet channel 411 to the first chamber 111; the second one-way valve 512 is disposed corresponding to the first liquid outlet 122, so that the fluid at the first liquid outlet 122 flows unidirectionally in a direction from the first chamber 111 to the liquid outlet channel 412; the third one-way valve is disposed corresponding to the second liquid inlet 123, so that the fluid at the second liquid inlet 123 flows unidirectionally in a direction from the liquid inlet channel 411 to the second chamber 113; the fourth one-way valve is disposed corresponding to the second liquid outlet 124, so that the fluid at the second liquid outlet 124 flows unidirectionally in a direction from the second chamber 113 to the liquid outlet channel 412.

Specifically, the cylinder 100 is provided with first installing holes 134, the number of the first installing holes 134 is four, and the four first installing holes 134 are disposed to correspondingly communicate with the first liquid inlet 121, first liquid outlet 122, the second liquid inlet 123 and the second liquid outlet 124, respectively; the cover 400 is provided with second installing holes 414, the number of the second installing holes 414 is four, and the four second installing holes 414 are disposed corresponding to the four first installing holes 134 respectively, and two of the four second installing holes and corresponding two first installing holes are in communication with the liquid inlet channel 411, and the other two second installing holes and corresponding two first installing holes are in communication with the liquid outlet channel 412. After the snap-fit installation between the cylinder 100 and the cover 400, the first installing holes 134 communicate with the second installing holes 414 to form accommodating spaces configured to install the one-way valves.

According to a pressure-pump cartridge 10 provided by this embodiment, a working principle of the pressure-pump cartridge 10 is as follows:

During installation, the piston 320 enters the first chamber 111 through the first opening 125, and then enters the piston chamber 112 under the guidance of the first guide surface 117, and is in sealing fit with the piston chamber 112, so as to divide the working chamber 110 of the cylinder 100 into two independent sub-chambers. Since there are formed the first liquid inlet 121 and the second liquid inlet 123 by injection molding or perforation on the first inner wall 114 corresponding to the first chamber 111, there will be burrs at the first liquid inlet 121 and the second liquid inlet 123. By disposing the first chamber 111 to be in clearance fit with the piston 320, the piston 320 is prevented from coming into contact with the burrs when passing through the first chamber 111 and entering the piston chamber 112, which in turn prevents the burrs from damaging the rubber ring 322 of the piston 320, thereby avoiding the damage to the rubber ring 322 to affect the sealing effect.

When in use, the piston 320 reciprocates under the driving of the power structure, so as to change the volume size of the first sub-chamber and the second sub-chamber. When the piston 320 moves toward the direction close to the first chamber 111, the volume of the first sub-chamber becomes smaller, and the fluid in the first sub-chamber is squeezed and passes through the first liquid outlet 122 into the liquid outlet channel 412, so as to perform infusion; the volume of the second sub-chamber becomes larger, and the fluid in the liquid inlet channel 411 enters the second sub-chamber through the second liquid inlet 123. When the piston 320 moves toward the direction close to the second chamber 113, the volume of the first sub-chamber becomes larger, and the fluid in the liquid inlet channel 411 enters the first sub-chamber through the first liquid inlet 121; the volume of the second sub-chamber becomes smaller, and the fluid in the second chamber 113 enters the liquid outlet channel 412 through the second liquid outlet 124, so as to perform infusion.

The pressure-pump cartridge 10 provided by this embodiment has at least the following advantages:

The embodiment of the present application provides a pressure-pump cartridge 10, which, by providing a first liquid inlet 121 and a first liquid outlet 122 that communicate with a first sub-chamber as well as a second liquid inlet 123 and a second liquid outlet 124 that communicate with a second sub-chamber, realizes a continuous infusion of the pressure pump and has excellent use effect. At the same time, by providing the first liquid inlet 121 and the first liquid outlet 122 at the first inner wall 114 corresponding to the first chamber 111, and disposing the first chamber 111 to be in clearance fit with the piston 320, it is avoided that the burrs damage the piston 320 during the installation process, thereby avoiding the problem of affecting the sealing performance of the piston 320, and the sealing effect is better.

This embodiment also provides a pressure pump, which includes the above-mentioned pressure-pump cartridge 10. Since the pressure pump includes the above-mentioned pressure-pump cartridge 10, it also has the beneficial effects of allowing continuous infusion, the good sealing performance of the piston 320, and more precise control of the infusion process.

The above are only specific embodiments of the present application, but the protection scope of the present application is not limited thereto, any variation or substitution readily conceivable by any skilled person who is familiar with the technical field disclosed in the present application should be covered by the protection scope of this application. Therefore, the protection scope of the present application should be subject to the protection scope of the claims.

What is claimed is:

1. A pressure-pump cartridge, including a cylinder, wherein the cylinder has a first chamber, a piston chamber and a second chamber that are in communication in sequence; and the cylinder has a first inner wall corresponding to the first chamber and a second inner wall corresponding to the second chamber; the first inner wall is provided with a first liquid inlet and a first liquid outlet, and the second inner wall is provided with a second liquid inlet and a second liquid outlet; and the piston chamber is configured to be in sealing fit with a piston; an end of the first chamber remote from the piston chamber has a first opening which is configured for entry of the piston, the first chamber is configured to be in clearance fit with the piston, wherein the pressure-pump cartridge further comprises a first sealing structure disposed at the first opening, the first sealing structure is connected with the cylinder to close the first opening, and the first sealing structure comprises a first connecting member and a first sealing member connected to the first connecting member, wherein the first sealing member is located within the first chamber to close the first opening, and the first connecting member is fixedly connected to the cylinder, and wherein the first sealing structure also has a through hole for a piston rod to pass through, the through hole is provided to pass through the first connecting member and the first sealing member, the first sealing member is in sealing fit with the piston rod, wherein the pressure-pump cartridge further comprises a fastener, the cylinder is provided with a first connecting hole, and the first connecting member is provided with a second connecting hole, the fastener fits with both the first connecting hole and the second connecting hole, so as to fix the first connecting member to the cylinder.

2. The pressure-pump cartridge according to claim 1, wherein the cylinder has a third inner wall corresponding to the piston chamber; a first guide surface is provided between the first inner wall and the third inner wall, and the first guide surface is configured to guide the piston from the first chamber into the piston chamber.

3. The pressure-pump cartridge according to claim 2, wherein a distance from the first guide surface to an axis of the piston chamber gradually decreases along a direction in which the first chamber points to the piston chamber.

4. The pressure-pump cartridge according to claim 3, wherein the first guide surface comprises a tapered surface, and a taper angle of the tapered surface is a, with $30° \leq \alpha \leq 150°$.

5. The pressure-pump cartridge according to claim 2, wherein both ends of the first guide surface are connected with the first inner wall and the third inner wall, respectively.

6. The pressure-pump cartridge according to claim 1, wherein both the first chamber and the piston chamber are cylindrical, a radial dimension corresponding to the first chamber is r1, and a radial dimension corresponding to the piston chamber is r2, with $0.2 \text{ mm} \leq (r1-r2)$.

7. The pressure-pump cartridge according to claim 1, wherein the second chamber is configured to be in clearance fit with the piston.

8. The pressure-pump cartridge according to claim 1, wherein the numbers of the first connecting hole, the second connecting hole and the fastener are all multiple, and the first connecting holes, the second connecting holes and the fasteners are disposed in a one-to-one correspondence, the multiple first connecting holes are evenly distributed along a circumferential direction of the first opening.

9. The pressure-pump cartridge according to claim 1, wherein the cylinder further has a second opening communicating with the second chamber, and the pressure-pump cartridge further includes a second sealing structure disposed at the second opening; and the second sealing structure is connected with the cylinder to close the second opening.

10. The pressure-pump cartridge according to claim 1, wherein the pressure-pump cartridge further comprises a first one-way valve, a second one-way valve, a third one-way valve and a fourth one-way valve;

the first one-way valve is installed to the first liquid inlet, the second one-way valve is installed to the first liquid outlet, the third one-way valve is installed to the second liquid inlet, and the fourth one-way valve is installed to the second liquid outlet.

11. A pressure pump, comprising the pressure-pump cartridge according to claim 1.

12. The pressure-pump cartridge according to claim 1, wherein the pressure-pump cartridge further includes a cover connected below the cylinder, the cover has a liquid inlet channel and a liquid outlet channel, the liquid inlet channel communicates with both the first liquid inlet and the second liquid inlet, and the liquid outlet channel communicates with both the first liquid outlet and the second liquid outlet.

13. The pressure-pump cartridge according to claim 12, wherein the cylinder is provided with a snap-fit groove, and the cover is provided with a snap-fit protrusion that is in snap-connection with the snap-fit groove, the cylinder is connected with and fixed to the cover by a snap-connection between the snap-fit protrusion and the snap-fit groove.

14. The pressure-pump cartridge according to claim 12, wherein the cylinder is provided with first installing holes, the number of the first installing holes is four, and the four first installing holes are disposed to correspondingly communicate with the first liquid inlet, the first liquid outlet, the second liquid inlet and the second liquid outlet, respectively; the cover is provided with second installing holes, the number of the second installing holes is four, and the four second installing holes are disposed corresponding to the four first installing holes respectively; two of the four second installing holes and corresponding two first installing holes are in communication with the liquid inlet channel, and the other two second installing holes and corresponding two first installing holes are in communication with the liquid outlet channel; the first installing holes communicate with the second installing holes to form accommodating spaces configured to install one-way valves.

\* \* \* \* \*